(12) United States Patent
Levy et al.

(10) Patent No.: US 9,993,245 B2
(45) Date of Patent: Jun. 12, 2018

(54) SURGICAL TACKER WITH QUANTITY INDICATOR

(71) Applicant: VIA SURGICAL LTD., Moshav Amirim (IL)

(72) Inventors: Arie Levy, Ramat-Gan (IL); Lena Levin, Moshav Amirim (IL); Ofek Levin, Moshav Amirim (IL)

(73) Assignee: Via Surgical Ltd., Moshav Amirim (IL)

(*) Notice: Subject to any disclaimer, the term of this patent is extended or adjusted under 35 U.S.C. 154(b) by 299 days.

(21) Appl. No.: 14/199,200

(22) Filed: Mar. 6, 2014

(65) Prior Publication Data
US 2014/0257339 A1    Sep. 11, 2014

Related U.S. Application Data

(60) Provisional application No. 61/776,009, filed on Mar. 11, 2013.

(51) Int. Cl.
*A61B 17/064* (2006.01)
*A61B 17/08* (2006.01)
(Continued)

(52) U.S. Cl.
CPC .......... *A61B 17/068* (2013.01); *A61B 17/064* (2013.01); *A61B 17/0643* (2013.01);
(Continued)

(58) Field of Classification Search
CPC .............. A61B 17/064; A61B 17/0682; A61B 17/0644; A61B 17/0643; A61B 17/08;
(Continued)

(56) References Cited

U.S. PATENT DOCUMENTS 2,881,762 A    4/1959  Lowrie
3,212,502 A   10/1965  Myers
(Continued)

FOREIGN PATENT DOCUMENTS

EP    1 206 924 A1    5/2002
EP    1 721 575 A2   11/2006
(Continued)

OTHER PUBLICATIONS

International Search Report and Written Opinion dated Feb. 13, 2015, for corresponding International Patent Application No. PCT/IB2014/001572, filed Mar. 6, 2014 (17 pages).
(Continued)

*Primary Examiner* — Ryan J Severson
(74) *Attorney, Agent, or Firm* — Brown Rudnick LLP; Thomas C. Meyers

(57) ABSTRACT

The invention relates to tacking devices for use in minimally invasive surgery that have a quantity indicator on a distal end that can be seen through a scope and that show a number of fasteners remaining in the device. A surgeon can watch the delivery of fasteners while simultaneously seeing f a number of fasteners remaining. This allows a hernia mesh to be properly fixed into place without going astray during the delicate initial placement procedure and also for even spacing of the fasteners on the mesh. The patient's post-operative recovery progresses well, and excessive pain is avoided. Methods of the invention include viewing the surgical site via the scope while also viewing the indicator via the scope.

5 Claims, 14 Drawing Sheets

(51) Int. Cl.
 *A61B 17/10* (2006.01)
 *A61B 17/068* (2006.01)
 *A61B 90/00* (2016.01)

(52) U.S. Cl.
 CPC ...... *A61B 17/0644* (2013.01); *A61B 17/0682* (2013.01); *A61B 17/08* (2013.01); *A61B 2017/0645* (2013.01); *A61B 2017/0647* (2013.01); *A61B 2017/0648* (2013.01); *A61B 2090/0803* (2016.02); *A61B 2090/0807* (2016.02)

(58) Field of Classification Search
 CPC .......... A61B 17/068; A61B 2017/0648; A61B 2017/0645; A61B 2019/4836; A61B 2019/4815; A61B 2017/0647; A61B 17/0686; A61B 17/083; A61B 17/10; A61B 17/105; A61B 2017/0646; A61B 2017/0649; A61B 2017/07278; A61B 2090/0804; A61B 2090/0805; A61B 2090/0806; A61B 2017/0807
 See application file for complete search history.

(56) References Cited

U.S. PATENT DOCUMENTS

| | | | |
|---|---|---|---|
| 3,266,301 A * | 8/1966 | Sovatkin | A61B 3/16 600/404 |
| 4,069,825 A | 1/1978 | Akiyama | |
| 4,391,402 A * | 7/1983 | Campbell | A61B 17/0684 227/121 |
| 4,458,835 A * | 7/1984 | Li | A61B 17/0684 227/121 |
| 4,536,933 A | 8/1985 | Furutsu | |
| 4,809,695 A | 3/1989 | Gwathmey et al. | |
| 4,900,303 A | 2/1990 | Lemelson | |
| 4,950,285 A | 8/1990 | Wilk | |
| 5,037,433 A | 8/1991 | Wilk et al. | |
| 5,104,395 A | 4/1992 | Thornton et al. | |
| 5,123,913 A | 6/1992 | Wilk et al. | |
| 5,174,487 A | 12/1992 | Rothfuss et al. | |
| 5,242,457 A | 9/1993 | Akopov et al. | |
| 5,290,310 A * | 3/1994 | Makower | A61B 17/0057 128/DIG. 8 |
| 5,330,488 A | 7/1994 | Goldrath | |
| 5,356,064 A | 10/1994 | Green et al. | |
| 5,359,993 A * | 11/1994 | Slater | A61B 1/00062 116/216 |
| 5,364,002 A | 11/1994 | Green et al. | |
| 5,364,022 A | 11/1994 | Ganz | |
| 5,425,489 A | 6/1995 | Shichman et al. | |
| 5,582,616 A | 12/1996 | Bolduc et al. | |
| 5,626,587 A | 5/1997 | Bishop et al. | |
| 5,728,113 A | 3/1998 | Sherts | |
| 5,830,221 A | 11/1998 | Stein et al. | |
| 5,895,395 A | 4/1999 | Yeung | |
| 5,916,146 A | 6/1999 | Allotta et al. | |
| 5,964,394 A | 10/1999 | Robertson | |
| 5,968,044 A | 10/1999 | Nicholson et al. | |
| 6,423,079 B1 * | 7/2002 | Blake, III | A61B 17/1285 606/143 |
| 6,447,524 B1 | 9/2002 | Knodel et al. | |
| 6,638,286 B1 | 10/2003 | Burbank et al. | |
| 6,733,506 B1 | 5/2004 | McDevitt et al. | |
| 7,141,057 B2 | 11/2006 | Burbank et al. | |
| 7,338,502 B2 | 3/2008 | Rosenblatt | |
| 7,398,908 B2 | 7/2008 | Holsten et al. | |
| 7,431,730 B2 | 10/2008 | Viola | |
| 7,591,783 B2 | 9/2009 | Boulais et al. | |
| 7,594,923 B2 | 9/2009 | Fallin et al. | |
| 7,625,386 B2 | 12/2009 | Abe et al. | |
| 7,658,311 B2 * | 2/2010 | Boudreaux | A61B 17/07207 227/175.2 |
| 7,704,261 B2 | 4/2010 | Sakamoto et al. | |
| 7,708,180 B2 | 5/2010 | Murray et al. | |
| 7,776,066 B2 | 8/2010 | Onuki et al. | |
| 7,842,047 B2 | 11/2010 | Modesitt et al. | |
| 7,850,701 B2 | 12/2010 | Modesitt et al. | |
| 7,913,891 B2 | 3/2011 | Doll et al. | |
| 7,918,377 B2 * | 4/2011 | Measamer | A61B 17/1114 227/175.2 |
| 7,918,868 B2 | 4/2011 | Marshall et al. | |
| 7,959,640 B2 | 6/2011 | Kantsevoy et al. | |
| 8,034,076 B2 | 10/2011 | Criscuolo et al. | |
| 8,038,686 B2 * | 10/2011 | Huitema | A61B 17/0682 606/142 |
| 8,070,035 B2 | 12/2011 | Holsten et al. | |
| 8,075,572 B2 | 12/2011 | Stefanchik et al. | |
| 8,091,756 B2 | 1/2012 | Viola | |
| 8,114,099 B2 | 2/2012 | Shipp | |
| 8,132,705 B2 | 3/2012 | Viola et al. | |
| 8,157,146 B2 * | 4/2012 | Edoga | A61B 17/068 227/175.1 |
| 8,177,795 B2 | 5/2012 | Niese et al. | |
| 8,211,126 B2 | 7/2012 | Yeh et al. | |
| 8,216,272 B2 | 7/2012 | Shipp | |
| 8,277,373 B2 | 10/2012 | Maahs et al. | |
| 8,282,670 B2 | 10/2012 | Shipp | |
| 8,343,176 B2 | 1/2013 | Criscuolo et al. | |
| 8,535,339 B2 | 9/2013 | Levin et al. | |
| 8,733,616 B2 * | 5/2014 | Bailly | A61B 17/064 227/179.1 |
| 9,770,262 B2 * | 9/2017 | Clancy | A61B 17/3468 |
| 2002/0107530 A1 | 8/2002 | Sauer et al. | |
| 2003/0139752 A1 | 7/2003 | Pasricha et al. | |
| 2004/0098045 A1 | 5/2004 | Grafton et al. | |
| 2004/0138681 A1 | 7/2004 | Pier | |
| 2004/0204723 A1 | 10/2004 | Kayan | |
| 2006/0235443 A1 * | 10/2006 | Huitema | A61B 17/0682 606/142 |
| 2007/0045379 A1 | 3/2007 | Shelton | |
| 2007/0112361 A1 | 5/2007 | Schonholz et al. | |
| 2007/0179509 A1 | 8/2007 | Nagata et al. | |
| 2007/0250064 A1 | 10/2007 | Darois et al. | |
| 2007/0270637 A1 | 11/2007 | Takemoto et al. | |
| 2008/0091219 A1 | 4/2008 | Marshall et al. | |
| 2008/0097523 A1 | 4/2008 | Bolduc et al. | |
| 2008/0110958 A1 | 5/2008 | McKenna et al. | |
| 2008/0255591 A1 | 10/2008 | Harada et al. | |
| 2008/0314954 A1 * | 12/2008 | Boudreaux | A61B 17/07207 227/175.1 |
| 2009/0018554 A1 | 1/2009 | Thorne et al. | |
| 2009/0114233 A1 * | 5/2009 | Edoga | A61B 17/068 128/898 |
| 2009/0222083 A1 | 9/2009 | Nguyen et al. | |
| 2010/0069930 A1 | 3/2010 | Roslin et al. | |
| 2010/0094248 A1 | 4/2010 | Nguyen et al. | |
| 2010/0096435 A1 * | 4/2010 | Fuchs | A61B 17/1114 227/179.1 |
| 2010/0145361 A1 | 6/2010 | Francischelli et al. | |
| 2010/0160931 A1 | 6/2010 | Karpiel et al. | |
| 2010/0191283 A1 | 7/2010 | Foerster et al. | |
| 2010/0292710 A1 | 11/2010 | Daniel et al. | |
| 2010/0318107 A1 | 12/2010 | Mizrahy et al. | |
| 2010/0327042 A1 | 12/2010 | Amid et al. | |
| 2010/0331863 A2 | 12/2010 | Saliman et al. | |
| 2011/0092992 A1 | 4/2011 | Darois et al. | |
| 2011/0098728 A1 | 4/2011 | McDevitt et al. | |
| 2011/0118757 A1 | 5/2011 | Pierce | |
| 2011/0130774 A1 | 6/2011 | Criscuolo et al. | |
| 2011/0178534 A1 | 7/2011 | Whitman et al. | |
| 2011/0319932 A1 | 12/2011 | Avelar et al. | |
| 2012/0016389 A1 | 1/2012 | Kantsevoy et al. | |
| 2012/0089157 A1 | 4/2012 | Forsell | |
| 2012/0109132 A1 | 5/2012 | Ellis et al. | |
| 2012/0116424 A1 | 5/2012 | Lee et al. | |
| 2012/0191091 A1 * | 7/2012 | Allen | A61B 18/1206 606/52 |
| 2012/0193394 A1 | 8/2012 | Holcomb et al. | |
| 2012/0245629 A1 | 9/2012 | Gross et al. | |
| 2012/0248171 A1 | 10/2012 | Bailly et al. | |

(56) References Cited

U.S. PATENT DOCUMENTS

| | | | |
|---|---|---|---|
| 2012/0265218 A1 | 10/2012 | Chen et al. | |
| 2012/0310259 A1 | 12/2012 | Sorrentino et al. | |
| 2013/0012961 A1 | 1/2013 | Reeser | |
| 2013/0018394 A1 | 1/2013 | Gambale | |
| 2013/0186936 A1 | 7/2013 | Shelton, IV | |
| 2014/0257339 A1* | 9/2014 | Levy | A61B 17/068 606/139 |
| 2015/0351862 A1* | 12/2015 | Clancy | A61B 17/3468 600/424 |
| 2015/0360019 A1* | 12/2015 | Clancy | A61B 90/39 600/432 |

FOREIGN PATENT DOCUMENTS

| | | |
|---|---|---|
| EP | 1 759 812 A1 | 3/2007 |
| JP | 5-161655 A | 6/1993 |
| WO | 96/03925 A1 | 2/1996 |
| WO | 01/65997 A2 | 9/2001 |
| WO | 20091100242 A2 | 8/2009 |
| WO | 20111068533 A1 | 6/2011 |

OTHER PUBLICATIONS

Abhishek, et al., 2012, Laparoscopic Umbilical Hernia Repair: Technique Paper, ISRN Minimally Invasive Surgery, pp. 1-4, Article ID 906405.

Gillian, et al., 2002, Laparoscopic Incisional and Ventral Hernia Repair (LIVH): An Evolving Outpatient Technique, JSLS 6(4):315-322.

International Search Report and Written Opinion dated Jun. 20, 2013 in related international application PCT/IB12/02957, filed Dec. 17, 2012 (10 pages).

International Search Report and Written Opinion dated Oct. 29, 2013, for International Patent Application No. PCT/IB2013/000647, filed Feb. 15, 2013 (17 pages).

Nguyen, et al., 2008, Postoperative Pain After Laparoscopic Ventral Hernia Repair: a Prospective Comparison of Clips Versus Tacks, JSLS 12:113-116.

Web page <http://www.covidien.com/silsstitch/pages.aspx> accessed on Mar. 29, 2012 (2 pages).

Web page <http://www.lsisolutions.com/rd180deviceanatomy> accessed on Mar. 29, 2012 (1 page).

* cited by examiner

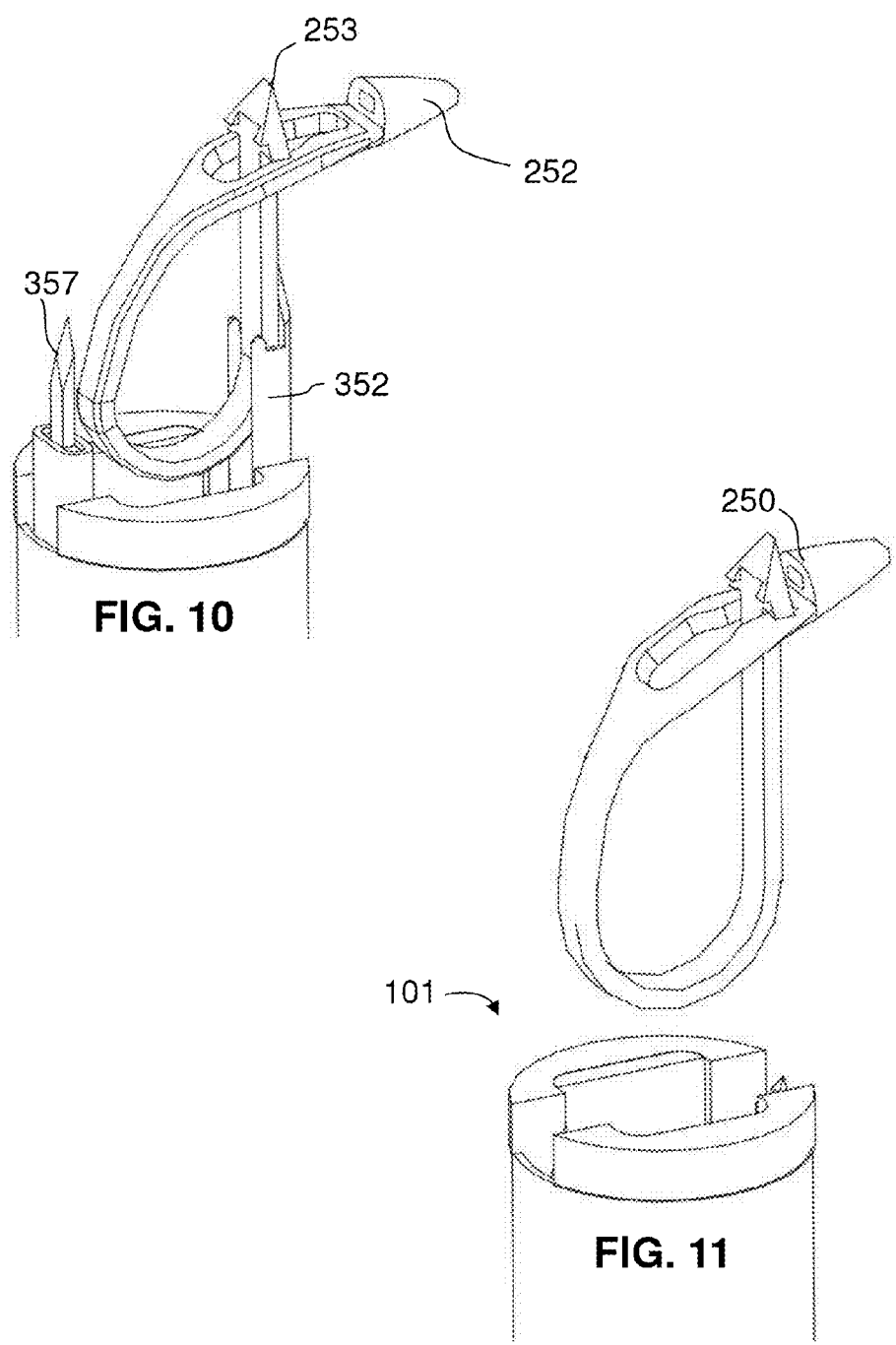

SURGICAL TACKER WITH QUANTITY INDICATOR

CROSS-REFERENCE TO RELATED APPLICATION

This application claims the benefit of, and priority to, U.S. Provisional Patent Application Ser. No. 61/776,009, filed Mar. 11, 2013, the contents of which are incorporated by reference.

FIELD OF THE INVENTION

The invention generally relates to surgical devices for use in minimally invasive surgery and particularly to devices that have a quantity indicator on a distal end.

BACKGROUND

Some surgical procedures involve delivering a series of clips such as tacks, staples, or sutures to a surgical site within a patient. For example, hernia repair can include fastening a type of prosthesis known as a hernia mesh to the tissue within a patient's abdomen. One approach involves performing a laparoscopic procedure to go into the abdomen with a surgical tacking device and deliver a series of clips to fix the mesh in place. A surgeon makes an incision and inserts surgical implements as well as an endoscope or laparoscope—a small telescope with a camera attached—to see the target site. These methods suffer from shortcomings that are associated with risks of complication and patient pain.

For example, while the mesh is being unfurled or is first tentatively positioned, it may be particularly important to deliver several fasteners in rapid succession. If the device runs out of fasteners during this step, the mesh could go astray in an unpredictable manner. The mesh may fold or flop into positions that are unmanageable and may result in bowel adhesions and post-operative pain. Unfortunately, if a surgeon looks away from the scope to examine the tacking device, that can also result in loosing orientation of the surgical field which result in prolonging of the operation and may also result in surgical errors. Also, once the mesh is first tacked into the proper position, the remaining fasteners ideally should be evenly distributed around the edges of the mesh. This can only happen if the surgeon knows the number of fasteners remaining and therefore the number of fasteners to place along each edge. If the mesh is not fastened properly—if an edge is not fastened well enough or if the positioning goes astray—the repair can fail and hernia recurrences may require the procedure to be repeated.

SUMMARY

The invention provides a surgical tacking device with an indicator that can be seen through the scope that shows a number of fasteners remaining in the device. A surgeon can watch the delivery of fasteners by a distal tip of the device while simultaneously seeing an indication of a number of fasteners remaining within the device. This allows the surgeon to, while placing a hernia mesh, see a direct indication of how many fasteners remain to be used. The surgeon thus knows if he is equipped to provisionally place the mesh and tack it down. Additionally, once a mesh is properly placed, the surgeon—without taking his eyes from the scope—can get a count of the number of fasteners remaining and thus decide how best to space the fasteners around the mesh. This allows a hernia mesh to be properly fixed into place without going astray during the delicate initial placement procedure. Since the surgeon knows how many fasteners are remaining, he can space those fasteners evenly about the hernia mesh and will not run out of fasteners with one edge of the mesh not yet fastened in place. Since this also allows a hernia mesh to be fastened into place with fasteners that are spaced evenly without repeatedly entering the surgical sites with multiple instruments, unwanted surgical complications are avoided. The patient's post-operative recovery progresses well, and excessive pain is avoided. Additionally sometimes hernia fasteners are misfired and fall down over the bowel. This can lead to bowel perforation and long term complications. The ability to count fired fasteners while visually inspecting the spot on the mesh that was targeted for fastening can give an indication if the fastener has indeed been misfired and whether the surgeon should search for it over the bowel and extract it out.

In certain aspects, the invention provides a surgical fastening device that has a handle with a trigger, an elongated shaft extending from the handle with a carrier portion disposed at a distal portion of the shaft, and a plurality of fasteners disposed within the carrier portion. The device includes an indicator on the distal portion of the shaft that shows a number of the plurality of fasteners that remain within the carrier portion. Preferably, operation of the trigger causes the device to deliver one of the plurality of the fasteners and to decrement by one the number indicated by the indicator. The indicator may have a linkage (e.g., a mechanical, electrical, digital, or optical linkage) between a visible marker disposed on a surface of the shaft and a location of a marker element disposed within the carrier portion. The indicator may include a visible marker, which can be configured to correspond to one of a set of graduations extending along the distal portion of the shaft. The indicator may include a visible marker configured to assume only certain discrete, pre-determined positions on a surface of the shaft. In some embodiments, the visible marker is offset from the graduations to compensate for parallax that arises when viewing the indicator (i.e., through a scope or camera device such as a laparoscope or endoscope). In certain embodiments, the indicator may include a ring that extends around the shaft and displaces along the shaft to indicate a number of fasteners remaining. This way, the ring may indicate the number when viewed from any approach angle.

In certain embodiments, the indicator includes a marker element disposed within the carrier portion and an electronic display. The electronic display may include a light (e.g., an LED), an LCD display, or similar on the distal portion. The electronic display may be, for example, a monitor coupled to an endoscopic camera (e.g., receiving information for the indicator via an electronic coupling to the marker element or by directly viewing the visible marker with the endoscopic camera).

In another embodiment, the indicator includes a color-coded portion. Any suitable color can be used. For example, a progressive color change can indicate a number of fasteners remaining (e.g., green is full; blue is partially full; red is almost empty (last 3 fasteners); and black is empty). Since the indicator is always located in the same spot (e.g., on the very distal tip), the surgeon does not need to direct the camera to a different location. Additionally, this embodiment may find particular application in settings where different surgeons are familiar with different numeral systems (e.g., where not all surgeons are primarily familiar with Arabic numerals).

In related aspects, the invention provides methods of performing surgical procedures that include using a surgical fastening device that has a handle with a trigger, an elongated shaft extending from the handle with a carrier portion disposed at a distal portion of the shaft, and a plurality of fasteners disposed within the carrier portion. The device includes an indicator on the distal portion of the shaft that shows a number of the plurality of fasteners that remain within the carrier portion. Preferably, methods include operating the trigger to deliver one of the plurality of the fasteners to a surgical site and to decrement by one the number shown by the indicator. Methods of the invention include viewing the surgical site via a scope (e.g., through an endoscope or on a monitor of a laparoscope) while also viewing the indicator via the scope.

BRIEF DESCRIPTION OF THE DRAWINGS

FIG. 10 shows a step in operation of the fastening device from FIG. 9.

FIG. 11 gives another step in operation of the fastening device from FIG. 9 & FIG. 10.

DETAILED DESCRIPTION

The invention provides devices and methods for minimally invasive (e.g., laparoscopic) surgical fixation. Any surgical fixation methods may be benefited by a device of the invention. In some embodiments, a device is provided for hernia repair by mesh fixation. Techniques and devices for hernia mesh fixation that may be modified to benefit through use of the invention include those described in Gillian, et al., 2002, Laparoscopic Incisional and Ventral Hernia Repair (LIVH): An Evolving Outpatient Technique, JSLS 6(4):315-322; U.S. Pub. 2013/0012961 to Reeser; U.S. Pub. 2012/0265218 to Chen; and in U.S. Pub. 2010/0318107 to Mizrahy, the contents of each of which are incorporated by reference in their entirety for all purposes.

A hernia mesh can be affixed to tissue through the use of sutures, pre-formed sutures, clips, tacks, anchors, staples, and other such fasteners. Such fasteners are referred to herein as clips. Exemplary fasteners are described in U.S. Pat. No. 8,343,176 to Criscuolo; U.S. Pat. No. 8,114,099 to Shipp; U.S. Pat. No. 5,830,221 to Stein; U.S. Pub. 2011/0130774 to Criscuolo; U.S. Pub. 2011/0022065 to Shipp; and U.S. Pub. 2010/0327042 to Amid, the contents of each of which are incorporated by reference.

Figure 1:
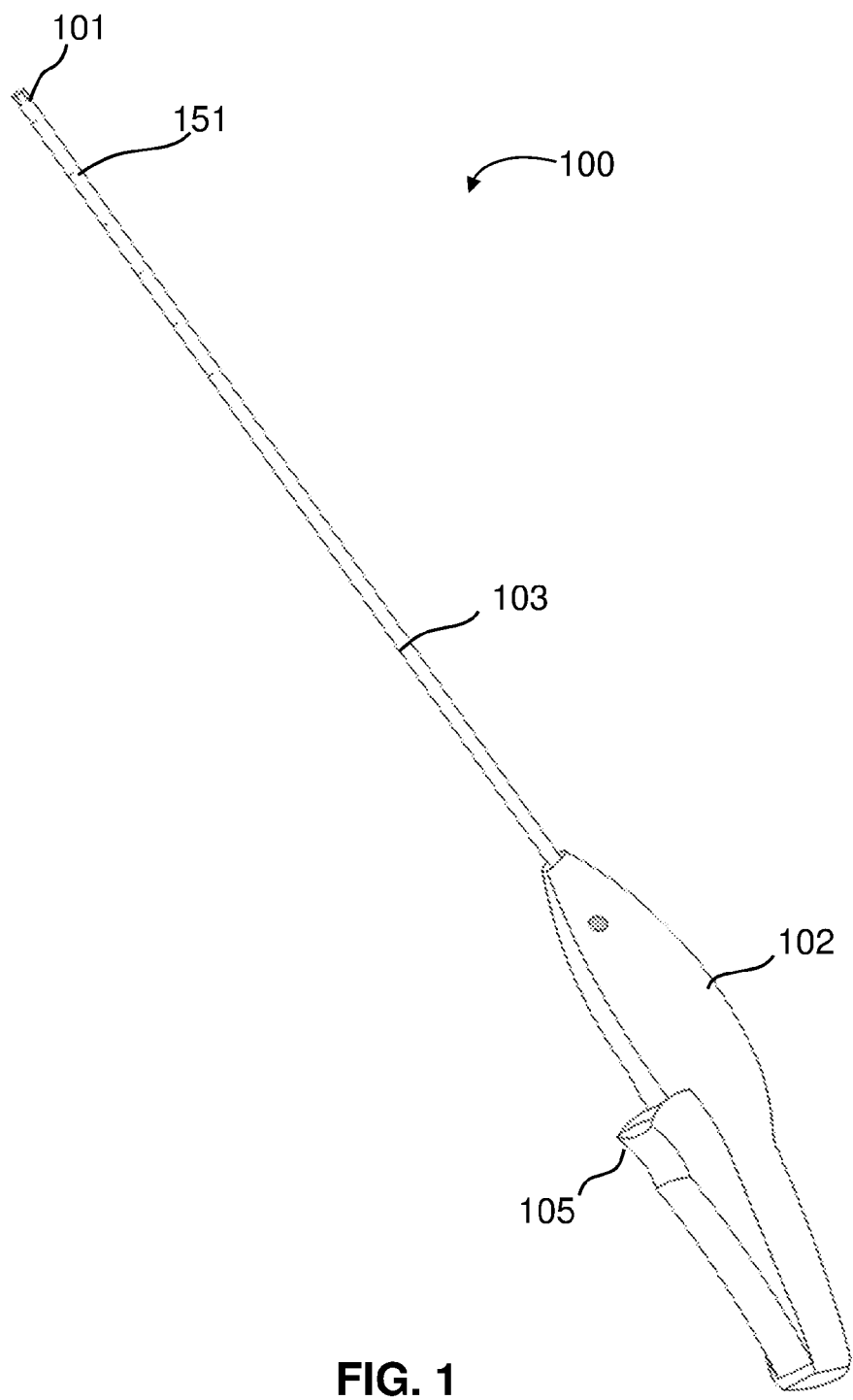
FIG. 1 depicts a fastening device for delivering fasteners of different sizes.

FIG. 1 depicts a fastening device 100 for delivering fasteners for hernia mesh fixation. Device 100 generally includes a handle 102 connected through shaft 103 to applicator section 101. Handle 102 will generally include a trigger 105. Squeezing trigger 105 delivers one fastener into tissue. Device 100 includes a carrier portion 151 for a holding plurality of fastener 250. The fastener carrier portion 151 is operably connected to the shaft 103 by any suitable attachment mechanism. For example, a portion of shaft 103 can extend into carrier portion 151 or a portion of carrier portion 151 can extend into shaft 103. Additionally, the fitting between shaft 103 and carrier portion 151 can be threaded, press-fit, use adhesives, or a combination thereof. Shaft 103 and carrier portion 151 can be co-molded or manufactured as a single piece. The connection between shaft 103 and carrier portion 151 is operable in that operation of trigger 105 delivers a fastener from carrier portion 151. Fastening device 100 can provide variable depth fastening by allowing for the switching of a cartridge-style carrier portion 151 wherein each cartridge contains a different length of fastener 250. Another way that device 100 can provided variable depth fastening is by allowing for the loading of different sizes of fastener 250 to a single device. Preferably, switching from one depth to another does not require any adjustment at the operation handle. For example, the first 4 of fastener 250 may be long with the rest being short (or a mixture of multiple sizes). In some embodiments, device 100 uses a stretchable fastener 250 (see, e.g., FIG. 18) and the fastener 250 penetration depth is adjusted through the stretching of fastener 250.

In some embodiments, carrier portion 151 is a replaceable cartridge. A replaceable cartridge can be provided that is pre-loaded with a selection of fastener 250. Replaceable cartridges adaptable for use with the invention are described in U.S. Pat. No. 5,356,064 to Green, the contents of which are incorporated by reference. One important benefit of indicator 141 relates to a replaceable cartridge. Where the cartridge carries the indicator of a number of clips remaining, replacing the cartridge does not require the indicator to be reset.

Figure 2:
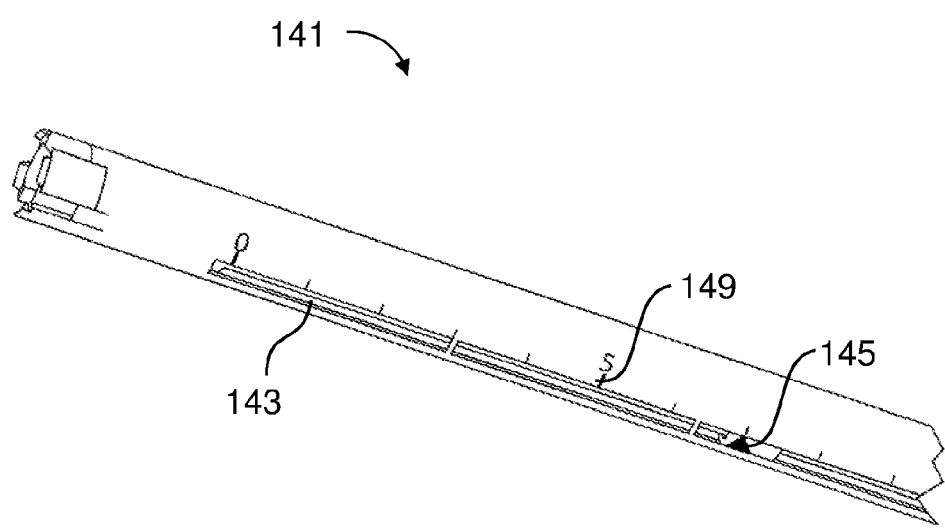
FIG. 2 shows an indicator on a surgical device.

FIG. 2 shows an indicator 141 that shows a number of fastener 250 remaining in device 100. Indicator 141 may be presented in any form that reveals a number of fasteners 250 remaining. The indicator may be positioned such that, when a surgeon is observing carrier portion 151 and applicator section 101 within a patient, the surgeon may also simultaneously observe indicator 141. For example, if a scope (e.g., laparoscope or endoscope) is being used to observe delivery of fasteners 250, indicator 141 is also visible through the scope. The mechanics of carrier portion 151 within shaft 103 preferably includes a marker element 947 (first shown in FIG. 4) that moves along shaft 103 each time a fastener 250 is delivered. As discussed in greater detail below with respect to FIG. 4, a location of marker element 947 corresponds to a present number of fasteners 250 in device 100. A location of marker element 947 can be used by indicator 141 to reveal a number of fasteners remaining in device 101. The indicator 141 may include a visible marker 145, which can be configured to correspond to one of a set of graduations 149 extending along the distal portion of the shaft. The indicator 141 may include a visible marker 145 configured to assume only certain discrete, pre-determined positions on a surface of the shaft. In some embodiments, the visible marker 145 is offset from the graduations 149 to compensate for parallax that arises when viewing the indicator (i.e., through a scope or camera device such as a laparoscope or endoscope).

In some embodiments, indicator 141 includes a visible marker 145 on carrier portion 151. In some embodiments, indicator 141 is anywhere on device 100, for example, at any position along shaft 103. In certain embodiments (not depicted), indicator 141 is an electronic device that relays information (e.g., a digital signal) to a receiver unit located outside of a patient (e.g., a computer or monitor). As shown in FIG. 2, indicator 141 may be embodied in a visible marker 145 configured to travel along a travel slot 143. Visible marker 145 may be an annular band, or ring, that extends around shaft 103. An annual band marker 145 may include a cylindrical piece of material (e.g., plastic, metal, other polymer) mounted on an extension that passes through travel slot 143.

In certain embodiments, indicator 141 includes a display element near applicator section 141. A display element can include a window or similar display that contains, for example, a numeral. The numeral can indicate the number of fasteners 250 remaining in device 100. The display element can be provided by a mechanically changing numeral (e.g., such as an odometer-style display wheel) or by an electronic display, such as an LCD, LED, or similar device. The displayed element can be a numeral, some other indicator (e.g., changing color, countdown needle, etc.), or a combination thereof. A color changing display offers a benefit of always being positioned at the same spot on the device, not requiring the surgeon to change viewing angle, and also is language-neutral. The display element can be fed by information from marker element 947. For example, a series of electrical contact points can be disposed within feeder cover 941 (see FIG. 5), and marker element 947 can provide an electrical contact point that completes a circuit with one of the points within cover 941, such that the completed circuit indicates a number of fasteners 250 in device 100. A display suitable for modification for use with the invention is described in U.S. Pat. No. 8,132,705 to Viola, the contents of which are incorporated by reference. Device 100 will generally deliver one or a plurality of fasteners 250 to a surgical site through the operation of a mechanical structures of handle 102 and shaft 103.

Figure 3:
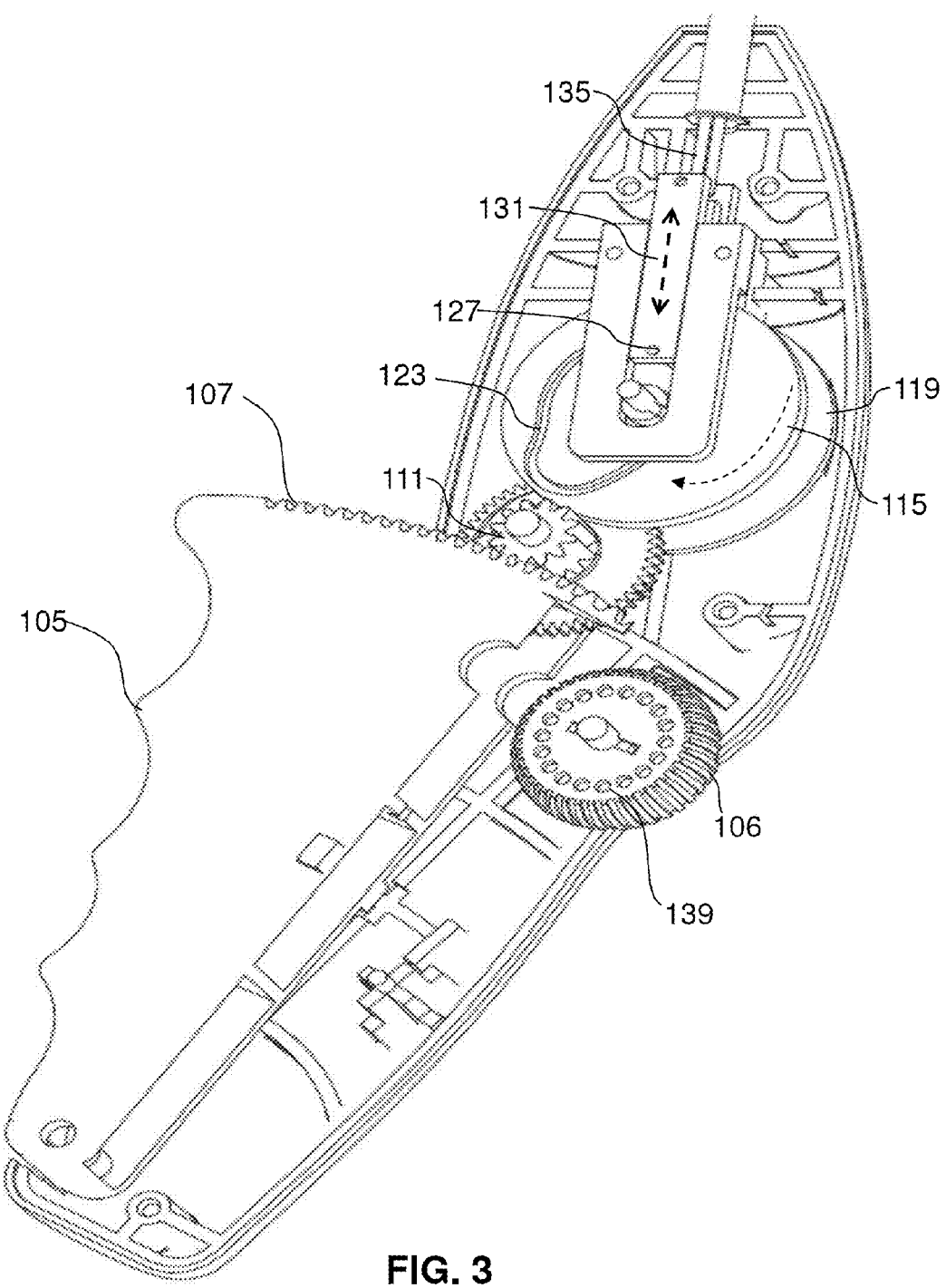
FIG. 3 gives a view of components of a handle of a fastening device.

FIG. 3 shows components of a handle of a fastening device. As can be seen in FIG. 3, one or more of push rod 135 are linked to one or more of translator bar 131. Translator bar 131 has a pin 127 fixed into a slot 123 of slot wheel 115. As shown in FIG. 3, applicator 100 includes a second slot wheel 119. Additional slot wheels may be included. The rotation of the slot wheel is driven through gear mechanism 111 by a geared face 107 of trigger 105.

By the relationship of these parts, when trigger 105 is squeezed, each of the slot wheels rotate. Because each slot (e.g., slot 123) is irregularly shaped (e.g., not a circle concentric with slot wheel 115), the corresponding translator bar translates independently relative to handle 102 and with acceleration defined by the disposition of the slot. The independent translation of translator bar 131 causes the independent translation of push rod 135 which (with reference to FIG. 7) cause the independent action of hook insertion needle 352 and loop insertion needle 357, as described above.

Embodiments of the invention provide methods of hernia mesh fixation that include using device 100, which includes indicator 141 on shaft 103 to show a number of fasteners that remain. Preferably, each operation of the trigger delivers and releases one fastener (e.g., closing it into a closed loop within the target tissue) and decrements the number shown by the indicator (e.g., by a color change or by repositioning the slider). Methods of the invention include viewing the surgical site via a scope while also viewing the indicator via the scope. Methods include replacing a cartridge with a full cartridge and not taking any additional steps to reset indicator 141. That is, since indicator 141 is on the cartridge and in linkage with fastener stack 955 (see, e.g., FIG. 4), indicator 141 will be default indicate a number of fasteners and not require intervention or a manual change. Additionally, methods of the invention allow for hernia mesh fixation and other procedure with greater dexterity and greater control over orientation of fasteners 250 in space and in tissue. Since a surgeon can see a number of fasteners remaining while applying a fastener, the surgeon can make an informed decision about where the next fastener should go. Surgical procedure like mesh fixation are complex. It occurs that a surgeon must position the mesh or target tissue using the tip of the device and then hold the mesh or tissue in place while applying the next one, two, or three fasteners. To be done properly, a surgeon preferably does not take his eyes off of the target site. Not knowing a number of fasteners that are ready to fire can compromise the deftness of the application.

In certain embodiments, the series of coordinated motions of the insertion needles, and the delivery of a fastener 250, is operated and coordinated electronically. For example, applicator device 100 can include servomotors operably connected to a governing circuit, chip, or combination thereof. A motor can drive the slot wheels. Or, motors can drive each push rod as governed by a chip executing instructions provided, for example, by a tangible, non-transitory computer memory such as, for example, a field-programmable gate array or a disc drive.

Where shaft 103 includes an articulation joint, articulation knob 106 controls the flexure of the joint. Knob 106 is rotated by a user (e.g., with a thumb). During the rotation, an articulation cable is wrapped around the knob's axis, pulling it toward the handle, articulating the joint. Knob 106 can include one or more of socket 139 adapted to fit a ball plunger in place once a desired degree of articulation is obtained.

Figure 4:
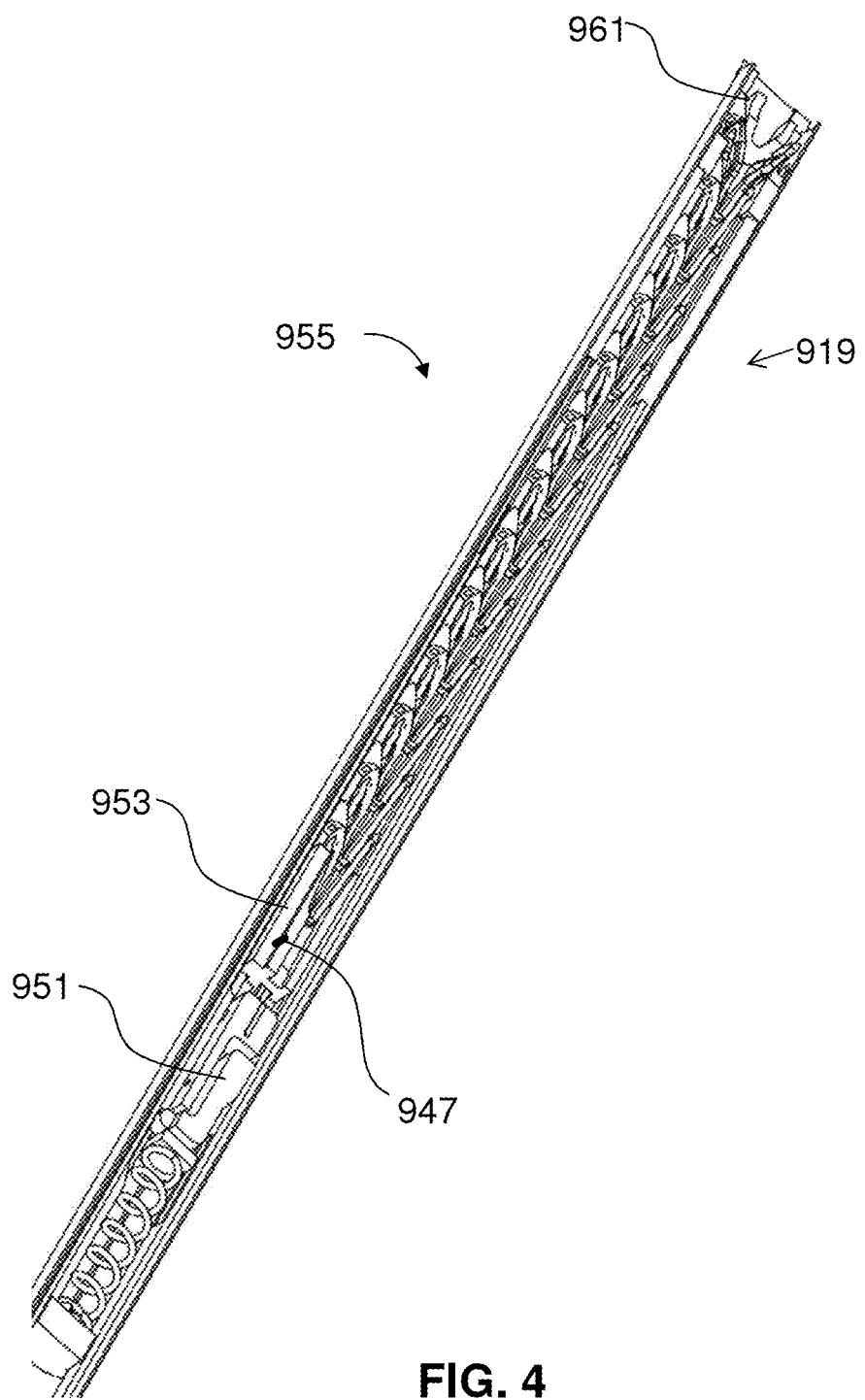
FIG. 4 illustrates the function of the fastener feeder.

FIG. 4 shows a cutaway view of applicator section 101 and fastener feeder mechanism 919. In operation, a comb driver assembly 951 first generates a single up and down stroke of a drive comb at the end of each application cycle (discussed and shown in more detail in connection with FIGS. 12-16 below). In FIG. 4, the drive comb extends under the plurality of fasteners 250, i.e., fastener stack 955. As a response to the stroke, the entire fastener stack 955 is pushed forward by the drive comb. During this process a hold comb (not shown in FIG. 4, see FIG. 5) prevents a downward movement of the pre-formed fasteners 250 in fastener stack 955.

In some embodiments, each time that a fastener is delivered, fastener support slide 953 advances by a fixed distance. Accordingly, in such embodiments, a position of fastener support slide within feeder mechanism 919 and thus shaft 103 is reflective of a number of fasteners remaining in device 100 to be delivered. The possible positions of fastener support slide 953 within shaft 103 may thus be quantized by a mechanical linkage relating the position of fastener support slide 953 to a number fasteners 250 remaining in fastener stack 955. In this way, a position of marker element 947 corresponds to a number of fasteners remaining in device 101.

Once the fasteners stack 955 is pushed upward (e.g., forward), the last fastener 250 is spread by the fastener spreader 961 and is positioned at collection slots 963 and 964 (visible in FIG. 5), ready to be collected by the insertion needles 352 and 357 (see FIG. 7) during the next application cycle. Each fastener 250 supports the next fastener 250 and prevents the lateral movement of its middle while it is pushed by drive comb 957. The last fastener 250 is supported by the fastener support slide 953. Fastener support slide 953 is pushed by the drive comb 957 together with the fasteners. A marker element 947 may protrude to the outer surface of the shaft, through a slot in feeder covers 941 (shown in FIG. 5), to indicate provide an indicator of a number of fasteners remaining in the device.

Figure 5:
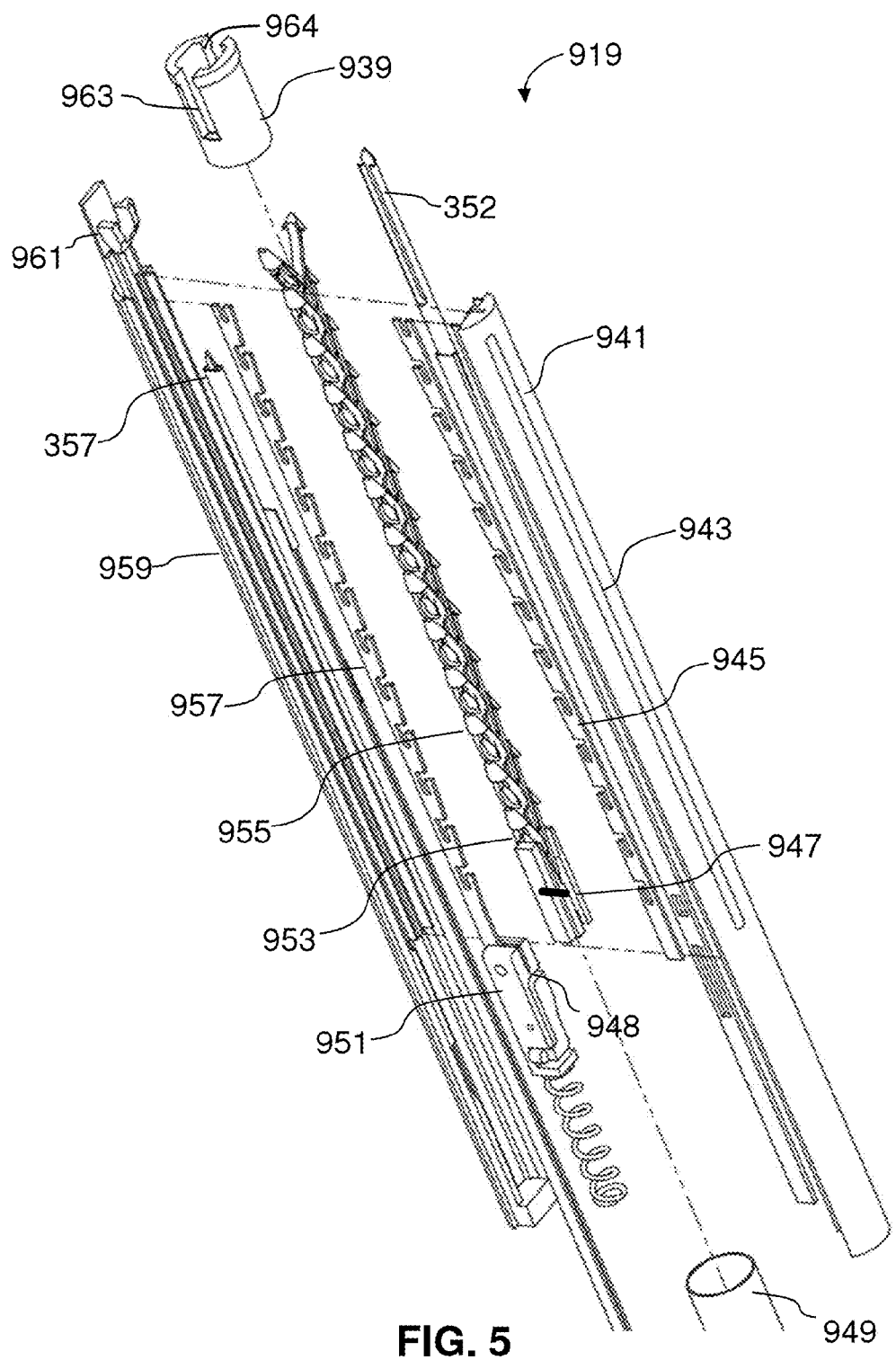
FIG. 5 is an exploded view of the structure of the fastener feeder mechanism.

FIG. 5 gives an exploded view of the fastener feeder mechanism 919. A hook insertion needle 352 lies under front feeder cover 941, which includes marker slot 943. Front cover 941 covers hold comb 945. Fastener stack 955 includes a plurality of fastener 250 extending from fastener support slide 953, which also includes marker element 947. Front cover 941 and back cover 959 covering and holding the fastener stack 955 and the fastener support 953, said front and back cover can be at least partially, substantially, or entirely encapsulated within the shaft cover 949 and terminate at shaft cap 939. Comb driver assembly 951 with comb driver hook 948 operates drive comb 957, as described below. Fastener feeder mechanism 919 includes loop insertion needle 357 disposed near fastener spreader 961. Shaft cap 939 includes a loop collection slot 963 and a hook collection slot 964. Fastener feeder mechanism 919 functions to deliver one fastener 250 from fastener stack 955 per operation of device 100.

Figure 6:
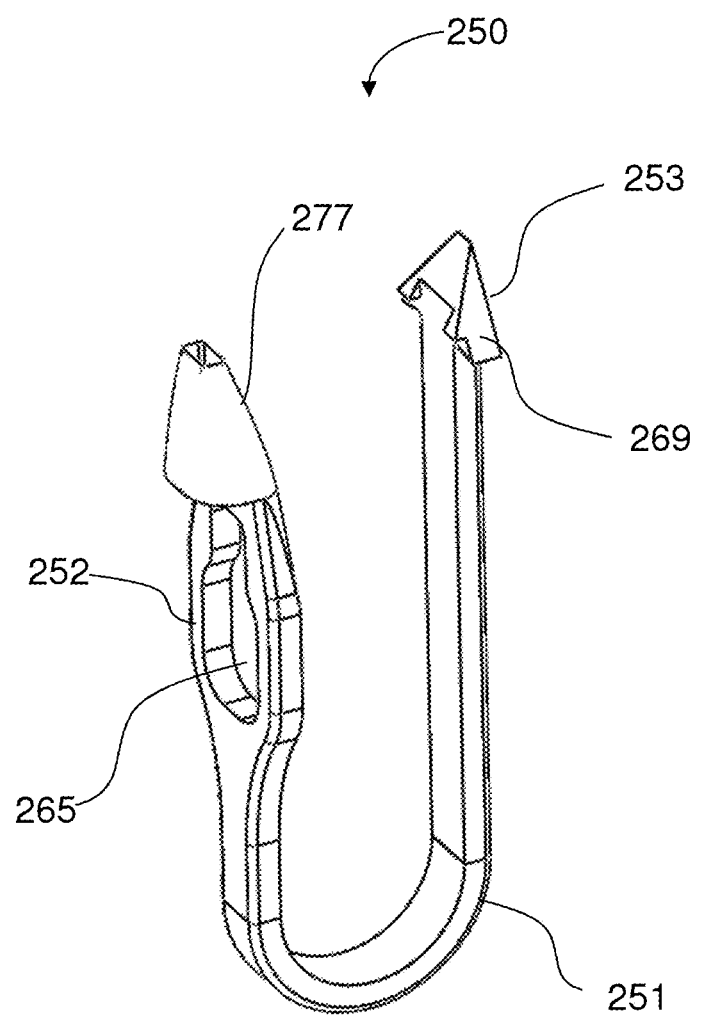
FIG. 6 depicts a pre-formed fastener according to certain embodiments.

FIG. 6 shows a fastener 250 according to certain embodiments. Preferably, fastener 250 is pre-formed and may have substantially the shape shown in FIG. 6. Generally, fastener 250 may include an extended body 251 having a first end 252 and a second end 253. First end 252 may include an opening 265 configured to capture and retain second end 253. FIG. 6 shows pre-formed fastener 150 in an open configuration, while FIG. 10 shows fastener 250 in a closed configuration. FIG. 11 shows fastener 250 in a locked configuration. Fastener 250 includes insertion slope 277 and at least one barb 269 that are dimensioned to operate with hook insertion needle 352 and loop insertion needle 357 of the applicator section 101 shown in FIG. 7.

Figure 7:
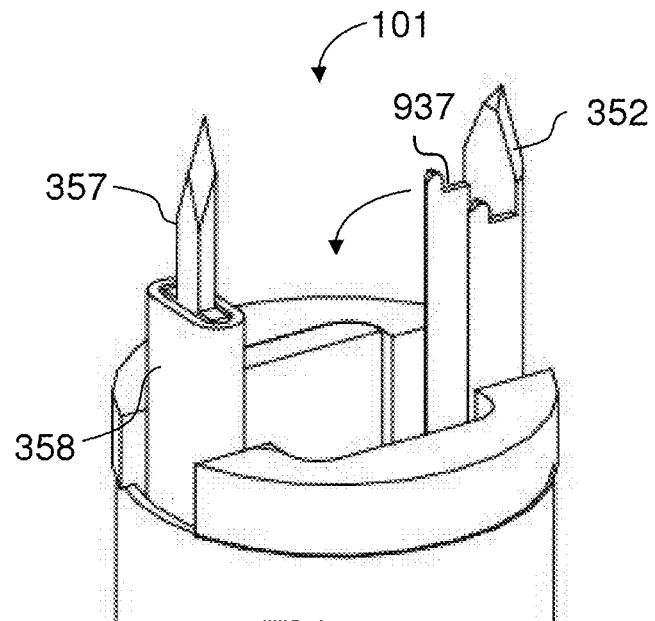
FIG. 7 reveals a applicator section.

FIG. 7 shows applicator section 101. Applicator section 101 provides loop insertion needle 357 and hook insertion needle 352. Loop insertion needle 357 may be disposed within a needle jacket 358. Discussed in more detail below, the function of needle jacket 358 may be to hold a portion of loop insertion needle 357 in a substantially straight configuration, while a portion of loop insertion needle 357 distal to the straight portion exhibits a curved configuration. Hook insertion needle 352 may include one or more catch slot 937 to catch or hold a portion of a fastener 250, such as barb 269 on second end 253.

Figure 8:
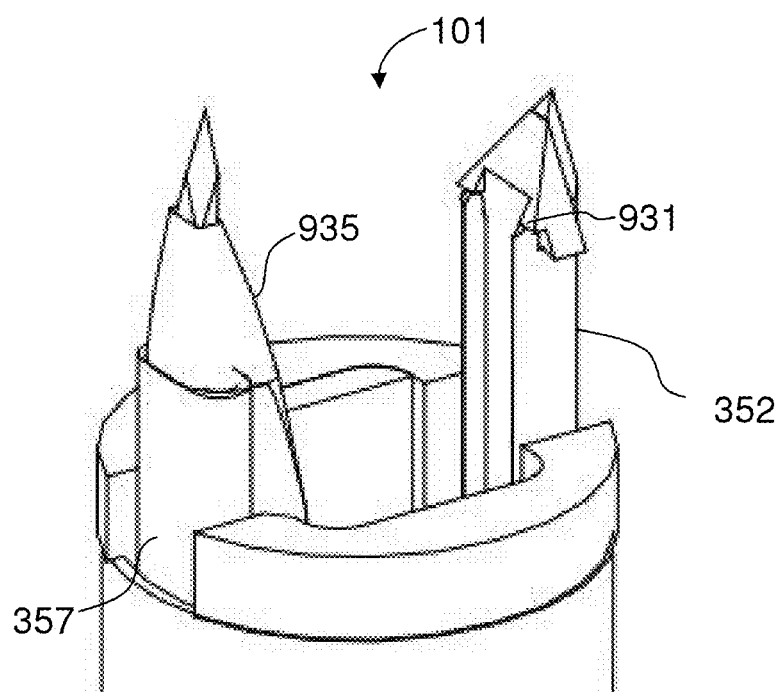
FIG. 8 shows a fastener loaded into the applicator section.

FIG. 8 shows an applicator section of a fastening device with fastener 250 according to certain embodiments. FIG. 7 shows the applicator section of FIG. 8, without a fastener 250. FIG. 7 shows loop insertion needle 357 and hook insertion needle 352. As shown in FIG. 8, the needle integration section 935 is shaped as a continuation of the needle tip in order to a allow penetration through the mesh and the tissue layers. Specifically, fastener 250 includes insertion slope 277 and the applicator includes a sloped needle integration section 935 that are dimensioned to cooperate to provide a substantially smooth, continual slope. Bulges 931 prevent the mesh fibers and the tissue from being caught between fastener 250 and hook insertion needle 352. As shown in FIG. 7, catch slot 937 is operable to hold the hook side of fastener 250 in place during penetration, e.g., by engaging barbs 269.

Figure 9:
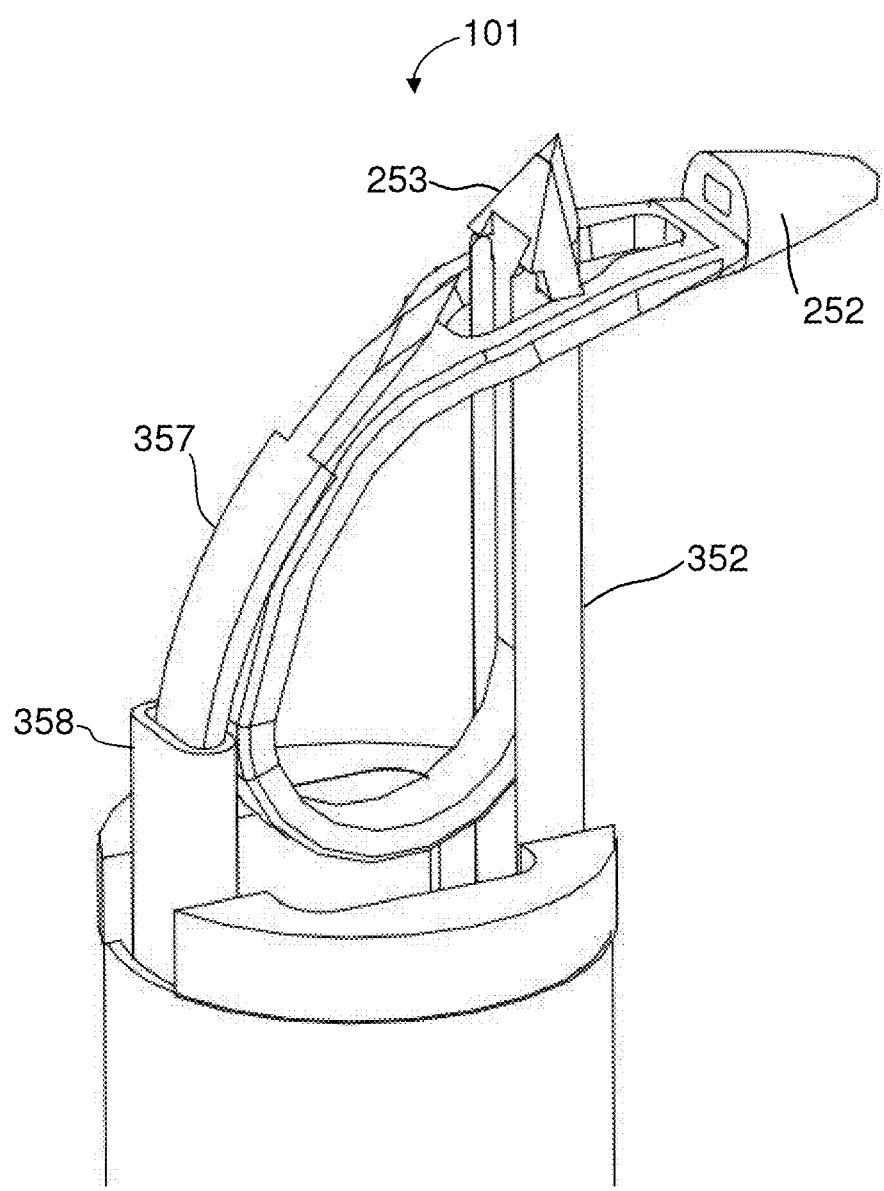
FIG. 9 depicts the operation of a fastening device of certain embodiments.

FIGS. 9-11 depict the operation of applicator section 101 of the applicator section depicted in FIG. 8. FIG. 9 shows an initial stage of operation. Hook insertion needle 352 and loop insertion needle 357 are fully engaged with first member 253 and second member 252, respectively, of fastener 250. Upon each operation of trigger 105, hook insertion needle 352 extends from a terminal end of shaft 103, as does loop insertion needle 357. Needle jacket 358 also extends from the terminal end. As shown in FIG. 9, the function of needle jacket 358 may be to hold a portion of loop insertion needle 357 in a substantially straight configuration, while a portion of loop insertion needle 357 distal to the straight portion exhibits a curved configuration. This allows fastener 250 to penetrate to a depth that is not otherwise limited by the geometry of device 100. Some prior devices can fasten deeper only by holding a fastener within a larger shaft or only by unspooling threaded suture material. Here, first end 252 and a second end 253 of fastener 250 may be any desired length and the action of hook insertion needle 352, loop insertion needle 357, and needle jacket 358 operate to fasten fastener 250 with tissue and release it there at a desired and variable depth.

As seen in FIG. 10, the loop is fully deployed and the hook partially penetrates the loop. In FIG. 11, hook insertion needle 352 holds the loop in place while the loop insertion needle 357 is retracted.

FIGS. 10-11C show locking and release of fastener 250. FIG. 9A shows hook insertion needle 352 pushing the hook through the loop. As shown in FIG. 10, since the hook is slightly wider than the loop's wide section, first member 253 is caught in second member 252 and removed from the hook insertion needle 352 once hook insertion needle 352 is retracted. FIG. 11 shows that, once tension is applied on the fastener, the hook slides to the narrow section of the hook. In this stage the fastener is locked.

As shown in FIGS. 9-11, delivering and fastening a fastener 250 may involve extending one or both ends of fastener 250 a distance from a terminal end of applicator section 101 along a path that includes both a straight portion and a curved portion. When a practitioner depresses trigger 105, loop insertion needle 357 extends from insertion tube 356 and interacts with first member 253 via loop interface hook 261. Hook insertion needle 352 has and maintains a substantially straight conformation as it assists in driving a hook end of fastener 250 into tissue. When loop insertion needle 357 is extended out from applicator section 101, it curves to guide the fastening of the fastener.

Fastener 250 is delivered by pushing each of its ends into tissue. Delivery is coordinated by the independent translation of push rods operably coupled to hook insertion needle 252 and loop insertion needle 357, which is triggered through the use of trigger 105. Coordination of delivery involves extending hook end of fastener 250 away from applicator section 101 while also extending loop end of fastener 250 and bringing the two ends of the fastener together (e.g., through the operation of a shape memory material in loop insertion needle 357). Methods include using the needles to drive fastener 250 into tissue and retracting the needles so they disengage from fastener 250 leaving it in place and fastened in a closed loop.

The invention thus provides methods for securing a medical prosthesis to tissue. Securing the prosthesis is accomplished through delivering a fastener to a target tissue that has a prosthesis applied to it, using applicator 100. Methods include inserting a distal portion of fastening device 100 into a patient's abdominal cavity through a trocar or through an incision. The distal end is pressed against the hernia mesh and a fastener is delivered through the tissue and hernia mesh and secured in place by pressing trigger 105 on handle 102. Shaft 103 is then removed.

Delivery according to the methods of the invention causes the first end of the body to mate with and be retained by the second end of the body, thereby forming the fastener into a closed configuration and securing the prosthesis to the tissue. The prosthesis can be secured by employing a fastening structure provided by the first and second members of fastener 250.

For hernia mesh 400 fixation, it is preferable that fastener 250 should be anchored to a fascia layer 401. Fascia is a layer of fibrous tissue containing closely packed bundles of collagen. Fascia provides a connective tissue that surrounds muscles, groups of muscles, blood vessels, and nerves. This is the layer to which surgeons affix a hernia mesh and the fastener design should form a strong anchor to that layer.

In each patient the thickness of the pre-peritoneal fat layer is different. For example, the first fascia layer in obese patients is significantly deeper than in slim patients. Some existing fixed-length hernia tacks favor shorter lengths so that, in slim patients, they will not penetrate all the way through the abdominal wall and to the skin. Fasteners that are too small, however, will not anchor into the fascia 401 in some sites or in obese patients for whom the pre-peritoneal fat layer is substantially thick. A fastening device of the invention is provided that can fix a hernia mesh despite variations in tissue with fasteners that pass beyond the hernia mesh by a controlled amount (e.g., between about 3 millimeters and 15 millimeters). By provided fasteners that extend only about a couple of millimeters past the hernia mesh, a fastening device of the invention provides good fixation to prevent recurrence of the hernia. By avoiding use of a fastener that is too long, post-operative pain is minimized. Considerations in fastener operation are discussed in Abhishek, et al., 2012, Laparoscopic Umbilical Hernia Repair: Technique Paper, ISRN Minimally Invasive Surgery, pp. 1-4, Article ID 906405, and in Nguyen, et al., 2008, Postoperative Pain After Laparoscopic Ventral Hernia Repair: a Prospective Comparison of Clips Versus Tacks, JSLS 12:113-116, the contents of each of which are incorporated by reference.

Figure 12:
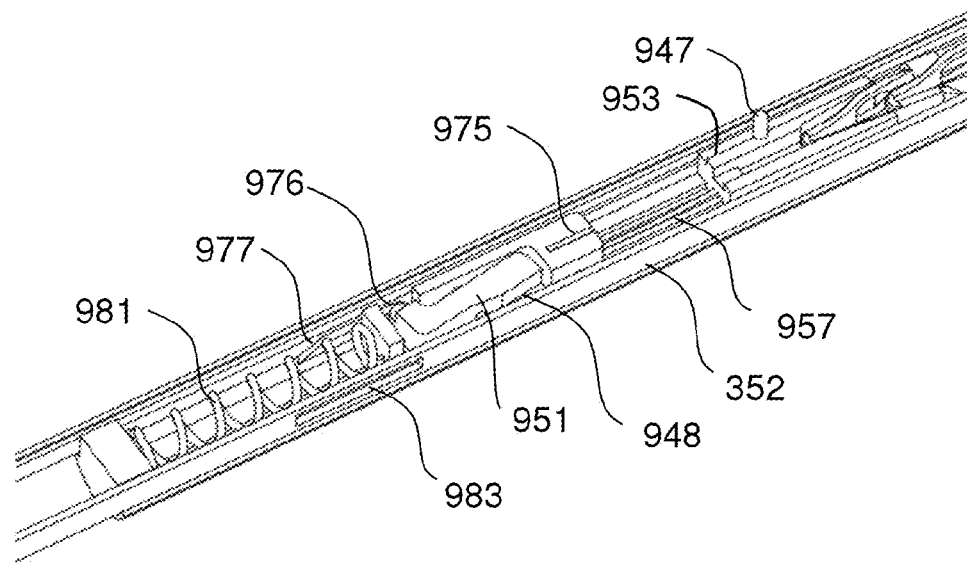
FIG. 12 depicts a step in the operation of the comb driver mechanism of a fastener feeder.
Figure 13:
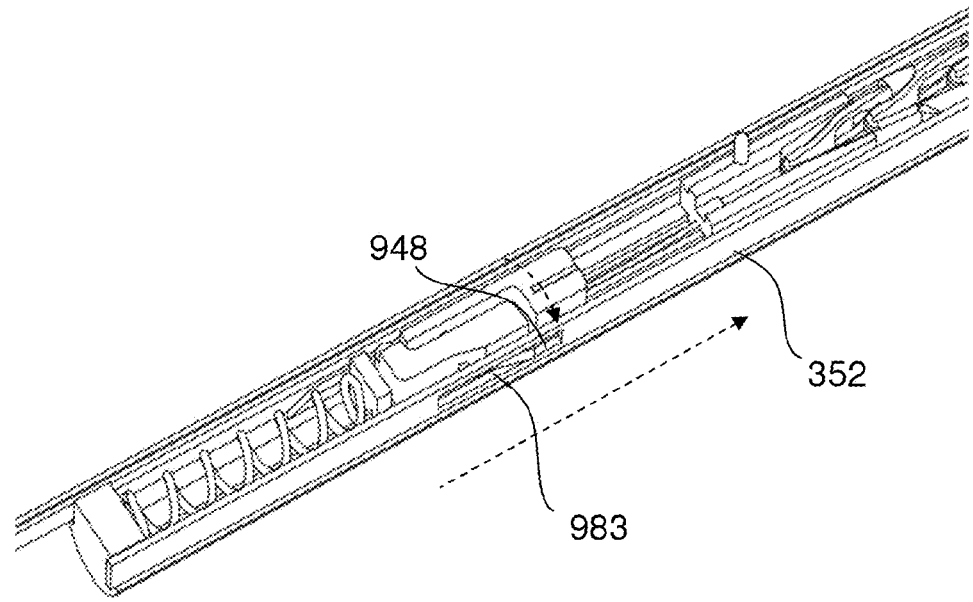
FIG. 13 shows another step in the operation of the comb driver mechanism.
Figure 14:
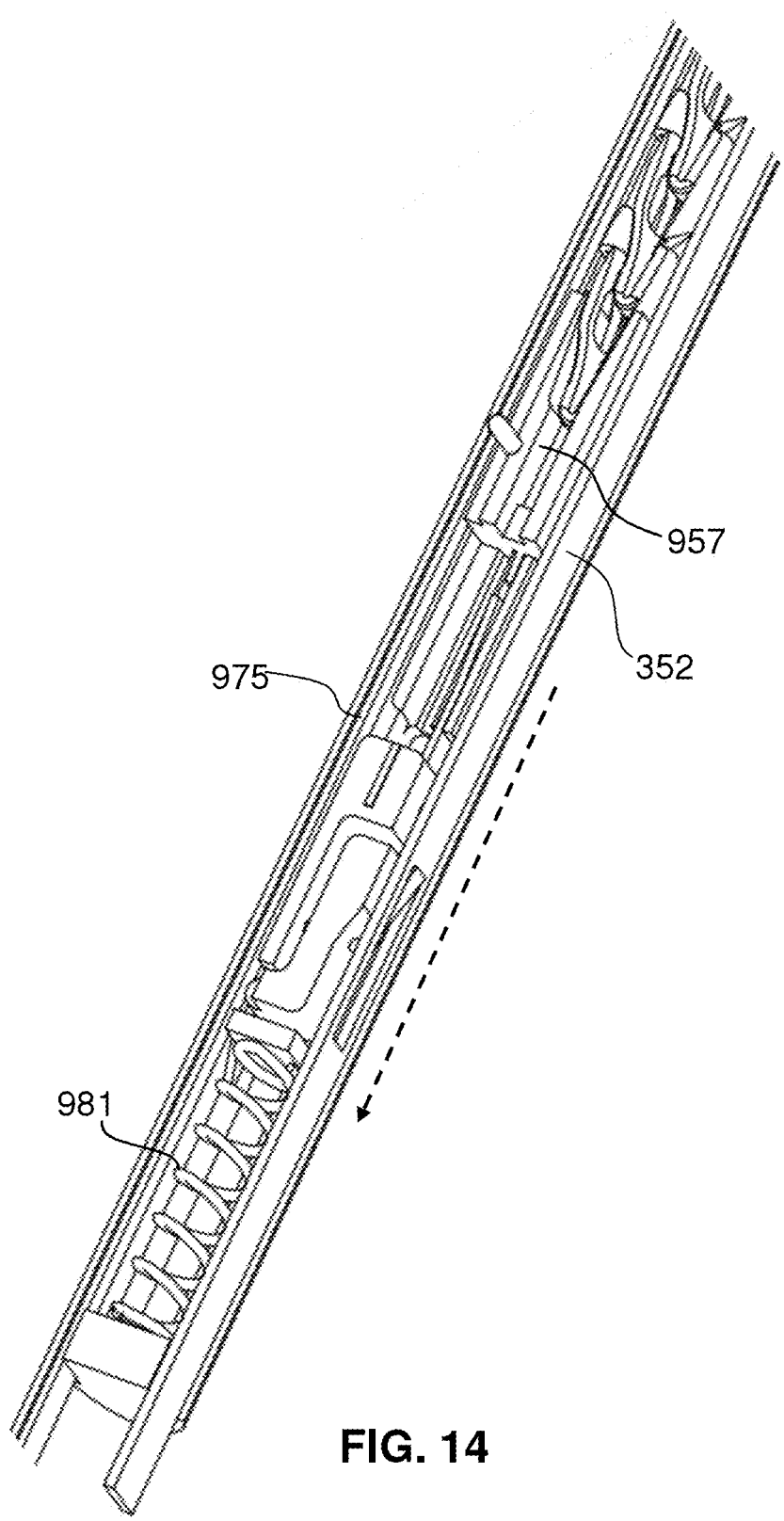
FIG. 14 gives a next step in the operation of the comb driver mechanism.
Figure 15:
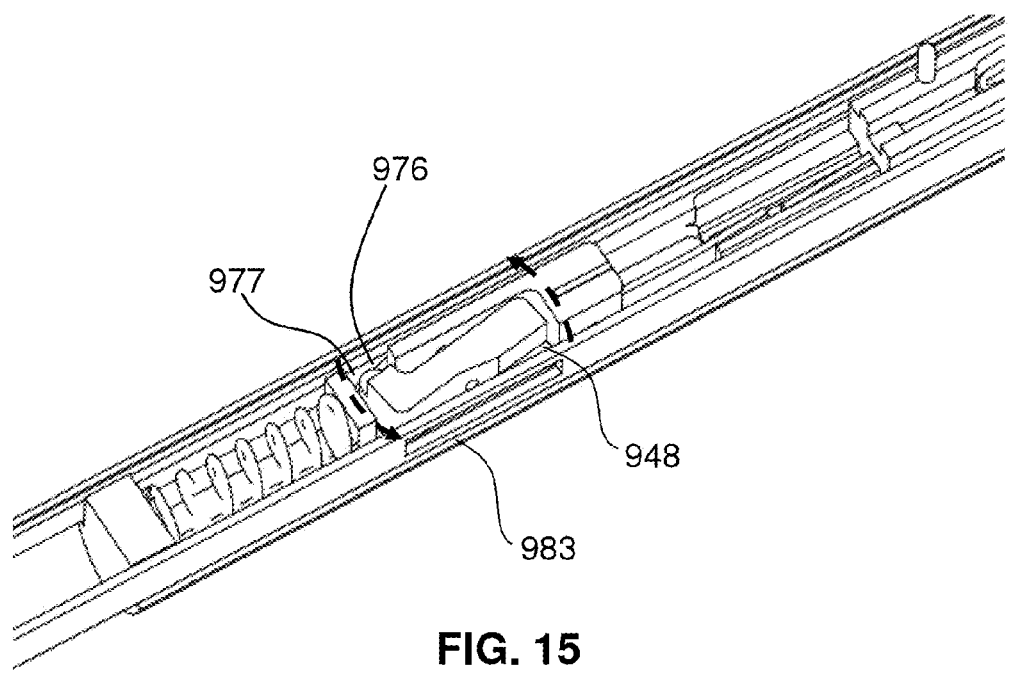
FIG. 15 illustrates a step in the operation of the comb driver.
Figure 16:
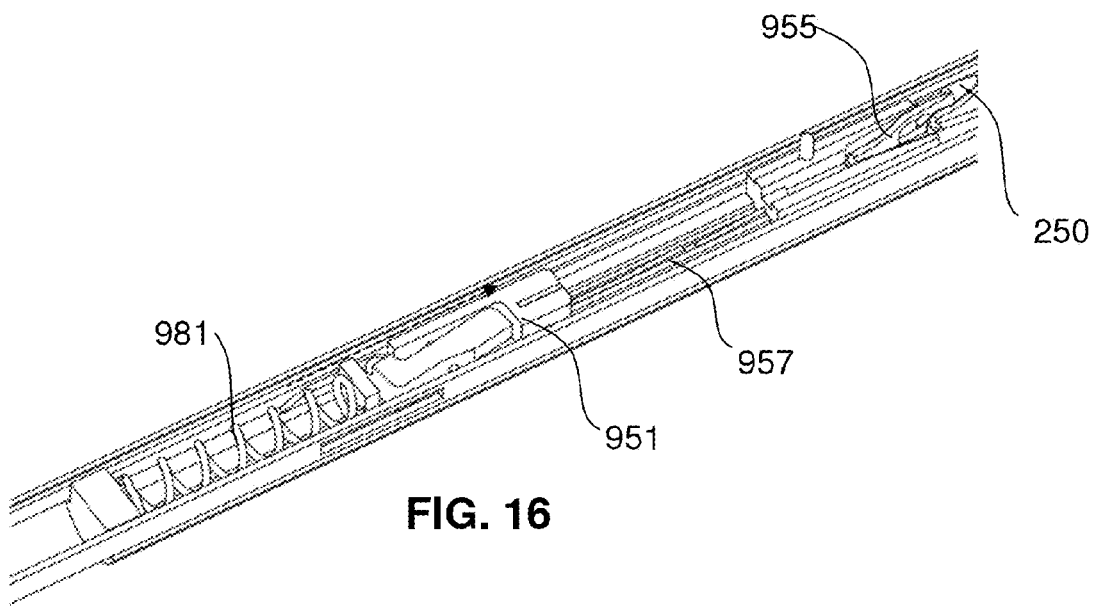
FIG. 16 shows a step in the operation of the comb driver mechanism.

FIGS. 12-16 depict the operation of the comb driver mechanism of fastener feeder mechanism 919. As seen in FIG. 12, comb driver assembly 951 provides a connection between comb driver hook 948 plus comb driver slide 975 and drive comb 957. Comb driver assembly 951, fastener support slide 953, or fastener stack 955 preferably has, somewhere thereon, marker element 947. Any suitable structure or element can be used for marker element 947. For example, marker element 947 may comprise a pin that engages part of an indicator 141. Marker element 947 may include an electrical contact point. In some embodiments, marker element 947 is itself a visible portion that is visible from an outside of shaft 103 and is viewed by a surgeon during a procedure. In certain embodiments, marker element 947 is one of fastener 250 (e.g., the last one, or most proximal one of fastener 250). As shown in FIGS. 12-16, marker element 947 will track the progress of drive comb 957 or a portion of the mechanics of the delivery mechanism during delivery. During delivery, release slope 977 and release bulge 976 release the comb driver hook from the hook insertion needle. Comb driver spring 981 can be seen by hook slot 983. The comb driver hook 948 is connected to the comb driver slide 975 by a flexible pin, allowing its rotation. FIG. 14 depicts a pulling back stage. At the final stage of the application cycle, the hook insertion needle 352 moves back while pulling the back the comb driver slide 975 and the drive comb 957 while pressing the comb driver spring 981. During this movement the comb teeth are engaged with pre-formed fasteners 250. FIG. 15 shows release. Once the release bulge 976 reaches the release slope 977, release bulge 976 is pushed laterally and removes the hook 948 out of the hook slot 983. FIG. 16 shows advancement of fastener 250. The compressed spring 981 pushes the comb driver 951 and the drive comb 957 forward while advancing the entire fastener stack 955.

In FIGS. 1-16, each fastener 250 is depicted as a pre-formed self-locking fastener, although other embodiments discussed herein are within the scope of the invention. For example, indicator 141 may be used with anchor-style fasteners 250, stretchable fasteners, staples, helical fasteners, or others.

Figure 17:
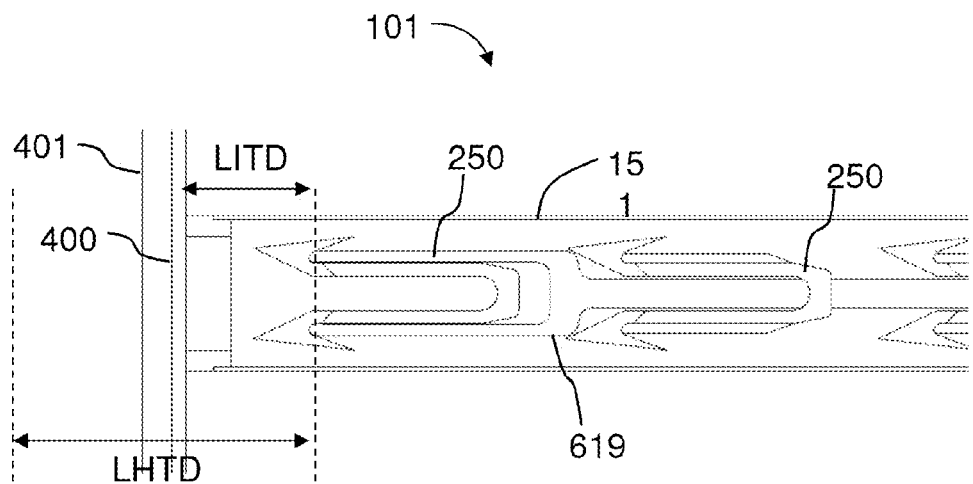
FIG. 17 shows a carrier loaded with long anchor-style fasteners.

FIG. 17 shows an applicator section 101 of fastening device 100 having a cartridge 151 for delivering a plurality of fastener 250 having an anchor style. Cartridge 151 has anchor-style fastener 250 of a long size disposed therein. Cartridge 151 can also accept anchor-style fasteners 250 of short or intermediate sizes, each separately or in any combination. Each operation of trigger 105 causes hammer 619 to travel a long-fastener hammer travel distance (LHTD). Marker element 947 may be disposed within the delivery mechanism on, for example, a proximal-most anchor. When delivering an anchor-style fastener 250 of a long size, hammer 619 will travel a long-fastener internal travel distance (LITD). As described in co-pending U.S. patent application Ser. No. 13/768,726 to Levy, et al., filed Feb. 15, 2013, and incorporated by reference in its entirety, anchor-style fasteners 250 of a variety of different size and even of mixed sizes may be delivered by the depicted mechanism. The anchor-style fasteners 250 are inserted into the tissue by pushing them forward using a reciprocal moving hammer 619. Hammer 619 scoops only the first anchor style fastener 250. An additional mechanism such as a spring positions each new fastener 250 in front of the hammer 619.

Figure 18:
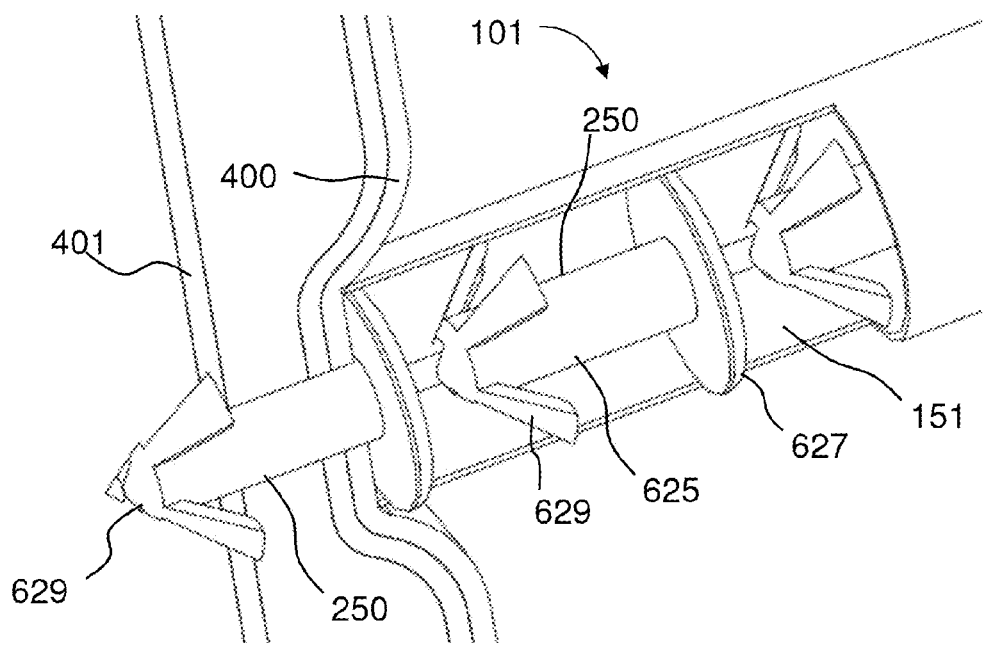
FIG. 18 gives a picture of a stretchable fastener.

FIG. 18 illustrates a device 100 for delivering a plurality of stretchable fastener 250. Stretchable fastener 250 generally includes an elastic material such as, for example, a poly-urethane, silicon, polyester, polyamide (e.g., nylon), polyolefin (e.g., polyethylene or polypropylene), poly-urethane carbonate, polydioxane, animal gut such as chromated catgut, metal such as steel, tantalum, or a shape memory metal. Marker element 947 may be disposed on or at a base of proximal-most fastener 250. Fastener 250 may include jacketed filaments such as twisted polyamide. This allows a surgeon to set the penetration depth of each individual stretchable fastener 250 at handle 102 without removing applicator section 101 from a patient. Once deeper penetration is set, the fastener tip 629 penetrates more into the tissue. Since the stretchable fastener 250 can be stretched, the final result is deeper penetration and longer stretchable fastener 250. As shown in FIG. 18, once the device is configured to penetrate deeper and a stretchable fastener 250 is delivered to tissue, the central core 625 of the stretchable fastener 250 is stretched to a deployed core length (DCL).

Figure 19:
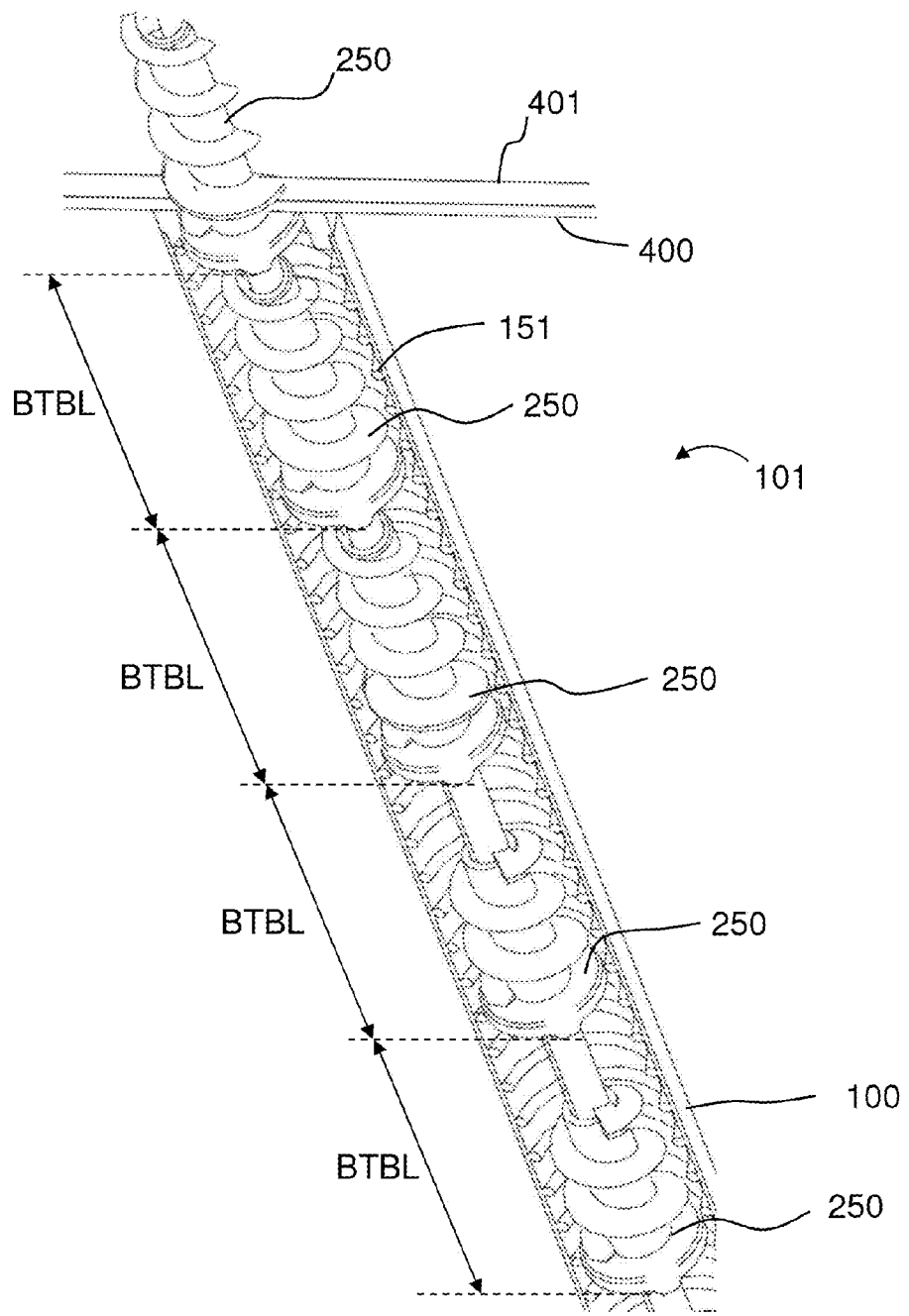
FIG. 19 shows a carrier loaded with tack-style fasteners.

FIG. 19 shows applicator section 101 with cartridge 151 loaded with tack-style fasteners 250 of a plurality of sizes. A marker element 947 may be disposed on or near the delivery mechanics such as, for example, on or near a base of proximal-most tack-style fastener 250. As shown in FIG. 19, at least two types of fastener 250 are arranged inside the device, e.g. the first three of fastener 250 are long of fastener 250 and rest are shorter. This allow the surgeon to apply different sized of fastener 250 without replacing a cartridge 151. If the surgeon doesn't want to apply any of a long fastener 250, each of the long fastener 250 can be ejected outside of the patient body before fastener 250 application. As before, the plurality of fastener 250 are arranged such that no adjustment at handle 102 mechanism is required. The base-to-base length (BTBL) between the base of each fastener is constant along a length of cartridge 151 regardless of a size of tack-style fasteners 250. For any version of a cartridge 151, the delivery mechanism displaces a fixed distance in a lateral direction along shaft 103. In a similar way to the anchor-style fastener 250 cartridge 151, the difference between the versions is the length in which the fastener 250 is moving inside and outside the device. Helical tack-style fasteners that may be adapted for use with device 100 are discussed in U.S. Pat. No. 8,282,670; U.S. Pat. No. 8,216,272; and U.S. Pat. No. 8,114,099, the contents of which are incorporated by reference. In some embodiments, a fastener may have tapered portions of a shaft, such as those shown in U.S. Pub. 2004/0098045.

As used herein, the word "or" means "and or or", sometimes seen or referred to as "and/or", unless indicated otherwise.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A surgical fastening device, comprising:
   a handle;
   a trigger disposed on the handle;
   an elongated cylindrical shaft defining an axis and comprising a proximal end and a distal end, the shaft connected at its proximal end to the handle;
   a carrier portion disposed at a distal portion of the shaft;
   a plurality of fasteners disposed within the carrier portion;
   a fastener support slide disposed in the carrier portion and in contact with a fastener nearest the proximal end of the shaft, the fastener support slide being translatable along the axis in discrete positions, each position corresponding to a different number of the plurality of fasteners that remain within the carrier portion;
   a visible marker disposed on a surface of the shaft and mechanically linked to the fastener support slide, the visible marker being translatable along the axis in discrete positions dependent on the position of the fastener support slide, each position corresponding to a different number of the plurality of fasteners that remain within the carrier portion; and
   an indicator on the distal portion of the shaft that shows a number of the plurality of fasteners that remain within the carrier portion based on the position of the visible marker in relation to the indicator, wherein one operation of the trigger causes delivery of one of the plurality of fasteners out of the distal end of the shaft and translation of the fastener support slide and visible marker by one position along the axis, and wherein the delivery of the one of the plurality of the fasteners and the position of the visible marker in relation to the indicator can be seen simultaneously through an endoscope when the elongated shaft of fastening device is inserted into an abdominal cavity of a patient through a surgical trocar.

2. The device of claim 1, further comprising graduations extending along the distal portion.

3. The device of claim 2, wherein the visible marker is configured to correspond to one of the graduations.

4. The device of claim 3, wherein the visible marker is offset from the graduations to compensate for parallax that arises when viewing the indicator through an endoscope.

5. The device of claim 1, wherein the carrier portion is a replaceable cartridge comprising the plurality of fasteners, the fastener support slide, the visible marker, and the indicator.

* * * * *